United States Patent [19]

Averill et al.

[11] Patent Number: 4,704,127

[45] Date of Patent: Nov. 3, 1987

[54] DUAL-GEOMETRY ACETABULAR CUP COMPONENT AND METHOD OF IMPLANT

[75] Inventors: Robert G. Averill, Ringwood; Alex Khowaylo, Allendale, both of N.J.

[73] Assignee: Osteonics Corp., Allendale, N.J.

[21] Appl. No.: 821,771

[22] Filed: Jan. 23, 1986

[51] Int. Cl.⁴ .............................................. A61F 2/34
[52] U.S. Cl. ........................................ 623/22; 623/18
[58] Field of Search ....................... 623/16, 22, 23, 20, 623/21

[56] References Cited

U.S. PATENT DOCUMENTS 3,808,606  5/1974  Tronzo ................................. 623/16
4,004,581  1/1977  Heimke et al. ...................... 623/22

FOREIGN PATENT DOCUMENTS 2645101  4/1978  Fed. Rep. of Germany ........ 623/22
1527498  10/1978  United Kingdom .................. 623/22

Primary Examiner—Richard J. Apley
Assistant Examiner—David Isabella
Attorney, Agent, or Firm—Samuelson & Jacob

[57] ABSTRACT

An acetabular cup has a shell component with an outer surface including a frusto-conical surface portion and a spherical surface portion and an acetabulum is prepared with an inner surface including a frusto-conical surface portion and a spherical surface portion, the spherical surface portions having essentially the same radius and the frusto-conical surface portions having relative dimensions such that upon nesting of the spherical surface portions in contiguous relationship, the frusto-conical portions engage one another in an interference fit to secure the shell component within the prepared acetabulum.

20 Claims, 4 Drawing Figures

DUAL-GEOMETRY ACETABULAR CUP COMPONENT AND METHOD OF IMPLANT

The present invention relates generally to prosthetic implant devices and methods and pertains, more specifically, to an acetabular cup component and the method by which the cup component is to be implanted within the acetabulum.

Acetabular cups routinely are employed to replace the socket provided by the natural acetabulum in the implant of hip joint prostheses. The securement of the acetabular cup within the bone of the hip joint has been accomplished through the use of cement. The shortcomings of the various available cements are well-documented and it would be advantageous to have available method and means by which an acetabular cup can be implanted and fixed within the acetabulum without the use of cement.

It is an object of the present invention to provide an acetabular cup component capable of being implanted and secured in place without the use of cement or another adhesive, and to provide the method by which the cup component is so secured.

Another object of the invention is to provide an acetabular cup component capable of being implanted and secured in place with an interference fit between the cup component and the surrounding bone.

Still another object of the invention is to provide a method by which an acetabular cup component is implanted and secured, utilizing an interference fit.

A further object of the invention is to provide an acetabular cup component capable of being implanted and secured in a well-defined position with a tight and stable interference fit.

A still further object of the invention is to provide a method by which the aforesaid well-defined position and tight and stable interference fit are attained within the limitations of the surgical environment.

The above objects, as well as still further objects and advantages, are attained by the present invention which may be described briefly as a shell component for use in an acetabular cup assembly of a prosthetic joint, the shell component being capable of implant into an acetabulum and securement therein by an interference fit, said shell component comprising: a lower rim; an upper top spaced upwardly in an axial direction a given distance from the lower rim; an outer surface having a generally frusto-conical surface portion extending upwardly from the lower rim to an intermediate location spaced approximately one-half the distance between the lower rim and the upper top, and a generally spherical surface portion extending upwardly from said intermediate location to the upper top, the frusto-conical surface portion making a shallow angle of about 6° with the axial direction. In addition, the invention includes the method for preparing the acetabulum for securement of the shell component therein by an interference fit.

The invention will be more fully understood, while even further objects and advantages will become apparent, in the following detailed description of preferred embodiments of the invention illustrated in the accompanying drawing, in which.

Figure 1:
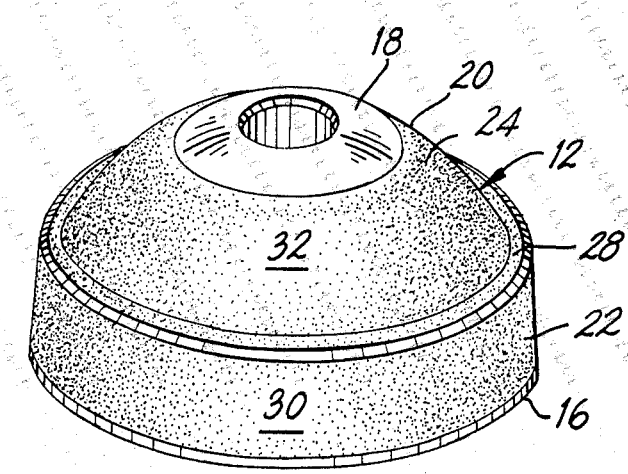
FIG. 1 is an exploded perspective view of an acetabular cup assembly including a shell component constructed in accordance with the invention.
Figure 1:
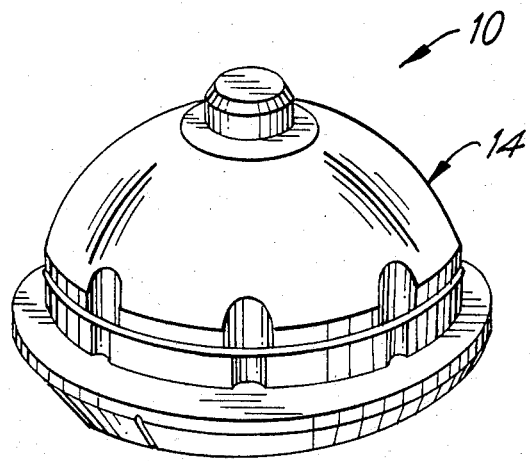

Referring now to the drawing and especially to FIG. 1 thereof, an acetabular cup assembly 10 is shown having a shell component 12 constructed in accordance with the invention, and a bearing component in the form of bearing insert 14. Initially, the shell component 12 will be implanted and secured within the acetabulum, as will be explained below, and the bearing insert 14 will be assembled with the shell component 12, interoperatively, in the manner described in a companion application entitled ACETABULAR CUP ASSEMBLY WITH SELECTIVE BEARING FACE ORIENTATION, filed of even date herewith, under Ser. No. 821,772.

Figure 2:
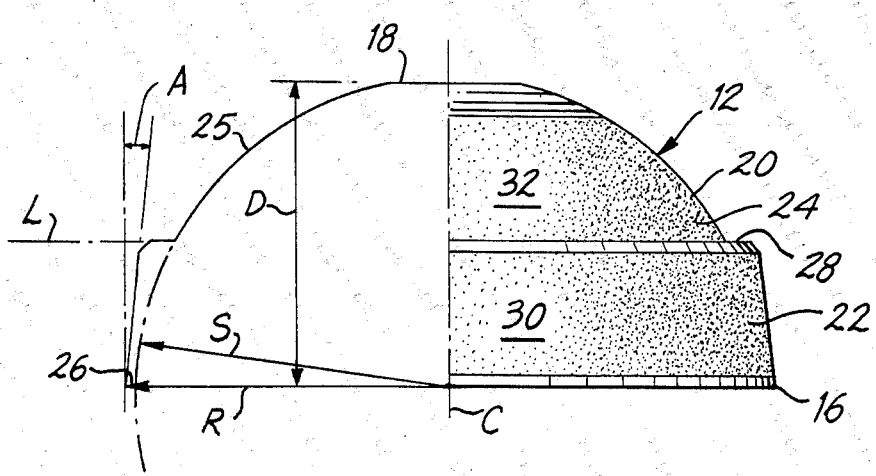
FIG. 2 is an enlarged, partially diagrammatic, elevational view of the shell component.

As best seen in FIG. 2, as well as in FIG. 1, shell component 12 includes a lower rim 16 and an upper top 18 spaced upwardly in an axial direction a given distance D from the lower rim 16. The outer surface 20 of the shell component 12 includes a frusto-conical surface portion 22 and a domed, spherical surface portion 24 which, together, establish a unique dual-geometry surface contour 25 along the outer surface 20 of the cup component 12.

The frusto-conical surface portion 22 extends upwardly along an essentially continuous profile, as depicted diagrammatically at the left side of FIG. 2, from lower rim 16 to a location L spaced upwardly from the rim 16 about one-half the distance D between the rim 16 and the top 18. The spherical surface portion 24 extends upwardly from the location L to the top 18. The frusto-conical surface portion 22 makes a shallow angle A with the axial direction, and the radius R of the frusto-conical surface portion 22 at the rim 16, as measured from the central axis C, is slightly greater than the radius S of the spherical surface portion 24, as seen at 26, so that the frusto-conical surface portion 22 is spaced radially outwardly from the spherical surface portion 24 in the surface contour 25 of the outer surface 20. A lateral surface portion 28 is placed at location L, between the frusto-conical and spherical surface portions 22 and 24. A textured surface finish 30 is provided along the frusto-conical surface portion 22 and a similar textured surface finish 32 is placed on an area of spherical surface portion 24, for purposes which will be described more fully hereinafter.

Figure 3:
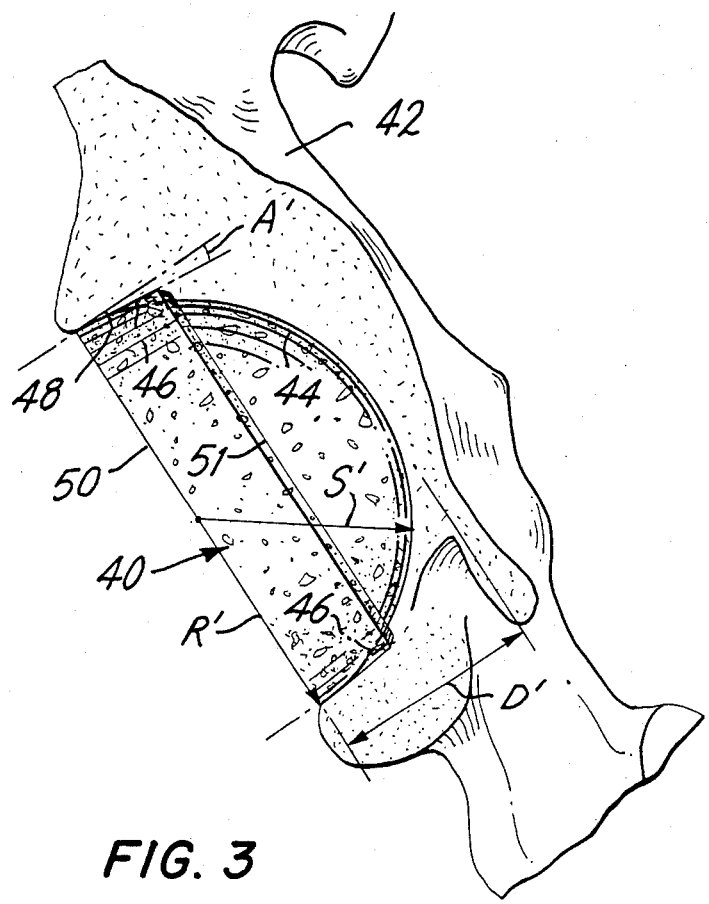
FIG. 3 is an illustration of a portion of a hip bone showing the preparation of the acetabulum in accordance with the invention.

Referring now to FIG. 3, the acetabulum 40 of a hip bone 42 has been provided with a surface contour of prescribed configuration, in accordance with the present invention, for the reception of shell component 12. Thus, acetabulum 40 is prepared by first forming spherical surface 44, as by reaming with a spherical reamer (not shown) to the full desired axial depth D' of the acetabulum. Initially, the spherical surface 44 will follow the contour illustrated by both the full lines and the phantom extensions 46 of FIG. 3. Then, a frusto-conical surface 48 is formed inwardly of the mouth 50 of the acetabulum 40, as by reaming with a frusto-conical reamer (not shown), thus creating an acetabulum 40 having a frusto-conical portion defined by surface 48 and a spherical portion defined by surface 44, as well as an intermediate lateral surface 51. The radius S' of the spherical surface 44 is the same as radius S of the spherical surface portion 24 of the shell component 12. Thus, the radius R' of the frusto-conical surface 48 at the mouth 50 of the acetabulum 40 is about the same as radius S' so that the radius R' is slightly smaller than radius R of the frusto-conical surface portion 22 of shell component 12. As in the shell component 12, the frusto-conical surface 48 makes a shallow angle A' with the axial direction, angle A' being essentially equal to angle A. Likewise, depth D' is essentially equal to distance D of the shell component 12.

It is noted that in the surgical environment the preparation of the acetabulum 40 is carried out with hand-held tools, so that it is ordinarily difficult to maintain the desired precision in the relationship between the required surfaces of the prepared acetabulum. However, the configuration of acetabulum 40 enables a sequence of operations which maintains precision. Thus, the initial formation of the spherical surface 44 is accomplished readily with precision through the use of an appropriately dimensioned spherical reamer. Then, by using the spherical surface 44 as a locating surface for the proper placement of a frusto-conical reamer, the frusto-conical surface 48 is located relative to the spherical surface 44 with the necessary degree of precision. Thus, the sequence of steps in the above-described method of the present invention establishes a prepared acetabulum 40 the configuration of which displays the precision necessary for the implant procedure which now will be described.

Figure 4:
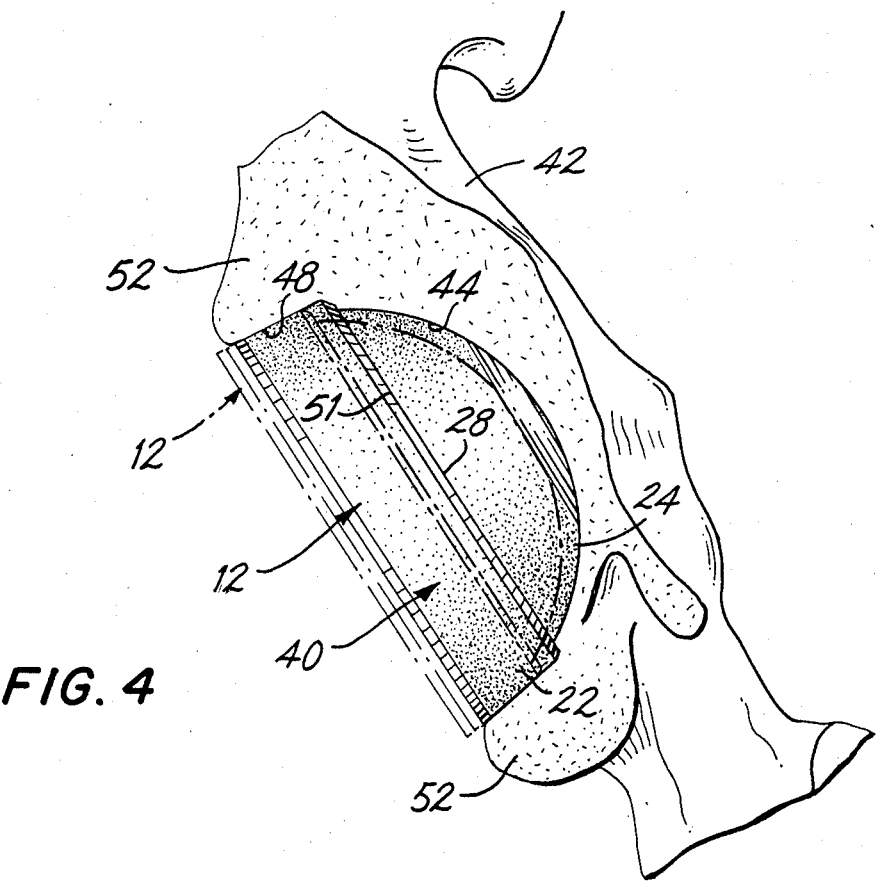
FIG. 4 is an illustration similar to FIG. 3, but showing the implant and securement of the shell component.

Turning now to FIG. 4, shell component 12 initially is placed in the prepared acetabulum 40 in the position shown in phantom. The taper provided by angles A and A' enables ease of placement of the shell component 12 within the prepared acetabulum 40 up to that position for starting the securement procedure. In addition, the taper promotes proper axial alignment of the shell component 12 within the acetabulum 40. Subsequently, the shell component 12 is impacted into the acetabulum 40 to achieve a tight, stable interference fit by virtue of the relative dimensions of the frusto-conical surface portion 22 of the shell component 12 and the frusto-conical surface 48 of the acetabulum 40. At the same time, the corresponding spherical surface portion 24 and spherical surface 44 are placed in a contiguous nested relationship.

It is noted that the frusto-conical surface 48 is located in the acetabular rim 52 and thus is placed within a region of optimal bone structure for the accommodation of the interference fit between the frusto-conical surface portion 22 of the shell component 12 and the frusto-conical surface 48. Thus, the shell component 12 is secured within the acetabulum 40 against rotation about the axial direction, against axial displacement and against rocking movements. The configuration of the outer surface contour 25 of shell component 12 assures such firm securement while requiring only minimal bone removal in the preparation of acetabulum 40. The textured surface finish 30 assists in fixing the shell component 12 in place, while the lateral surface portion 28, acting in conjunction with lateral surface 51, assists in deterring axial upward displacement of the shell component beyond the proper fully-seated position and assists in precluding rocking movements. The textured surface finish 32, as well as textured surface finish 30, promotes tissue ingrowth for further securement. In addition, location of the frusto-conical surface portion 22 of the shell component 12 within the acetabular rim 52 provides a transfer of the load placed on the shell component 12 resembling the natural load transfer.

Shell component 12 is manufactured in a range of sizes. Typically, the diameter of the spherical surface portion 44 will range from about 40 mm. to 72 mm. With the frusto-conical surface portion 22 extending along approximately one-half the distance D, an angle A of about 6° has been found to accomplish optimum results. The term "about 6°" is meant to encompass angles which can vary slightly from the nominal 6° while still accomplishing adequate results. Likewise, the term "approximately one-half the distance D" denotes the ability to depart slightly from the nominal one-half the distance D while still attaining adequate performance. It has been found that a difference of only about 0.5 mm. between the radius R of the frusto-conical surface portion 22 and the radius S of the spherical surface portion 24, when employed in combination with the aforesaid dimensions, is sufficient to accomplish an interference fit having the qualities outlined above without introducing deleterious or intolerable stress in the surrounding bone structure. Such a difference establishes a concomitant difference of about 0.5 mm between the radius R of the frusto-conical surface portion 22 of the shell component 12 and the radius R' of the frusto-conical surface 48 of acetabulum 40, to provide the desired interference fit.

It is to be understood that the above detailed description of preferred embodiments of the invention is provided by way of example only. Various details of design and construction may be modified without departing from the true spirit and scope of the invention as set forth in the appended claims.

The embodiments of the invention in which an exclusive property or privilege is claimed are defined as follows:

1. A shell component for use in an acetabular cup assembly of a prosthetic joint, the shell component being capable of implant into an acetabulum and securement therein by an interference fit, said shell component comprising:
   a lower rim;
   an upper top spaced upwardly in an axial direction a given distance from the lower rim;
   an outer surface having a generally frusto-conical surface portion extending upwardly along an essentially continuous profile from the lower rim to an intermediate location spaced approximately one-half the distance between the lower rim and the upper top, and a generally spherical surface portion extending upwardly from said intermediate location to the upper top, the frusto-conical surface portion making a shallow angle of about 6° with the axial direction.

2. The invention of claim 1 wherein the radius of the frusto-conical surface portion at the lower rim is slightly greater than the radius of the spherical surface portion.

3. The invention of claim 2 wherein the difference between the radius of the frusto-conical surface portion at the lower rim and radius of the spherical surface portion is approximately 0.5 mm.

4. The invention of claim 1 wherein the outer surface includes a generally lateral surface portion at the intermediate location.

5. The invention of claim 1 including a textured surface finish along the frusto-conical surface portion.

6. The invention of claim 5 including a further textured surface finish along the spherical surface portion.

7. An acetabular cup capable of implant into an acetabulum and securement therein by an interference fit, the acetabular cup having a lower rim, an upper top spaced upwardly in an axial direction a given distance from the lower rim, and an outer surface extending between the lower rim and the upper top and including a surface contour, said surface contour comprising:

a generally frusto-conical portion extending upwardly along an essentially continuous profile between the lower rim and an intermediate location spaced approximately one-half the distance between the lower rim and the upper top; and a generally spherical portion extending upwardly between said intermediate location and the upper top;

the frusto-conical portion making a shallow angle of about 6° with the axial direction.

8. The invention of claim 7 wherein the radius of the frusto-conical portion at the lower rim is slightly greater than the radius of the spherical portion.

9. The invention of claim 8 wherein the difference between the radius of the frusto-conical portion at the lower rim and the radius of the spherical portion is approximately 0.5 mm.

10. The invention of claim 7 wherein the surface contour includes a generally lateral portion at the intermediate location.

11. The invention of claim 7 including a textured surface finish along the frusto-conical portion.

12. The invention of claim 11 including a textured surface finish along the spherical portion.

13. In the method of implanting the shell component of claim 1 within a prepared acetabulum and securing the shell component therein with an interference fit, the steps of:

preparing the acetabulum to provide a prescribed configuration having a mouth, a depth extending inwardly in an axial direction and corresponding to the distance between the lower rim and the upper top of the shell component, and an inner surface including a generally frusto-conical surface portion extending inwardly from the mouth along an essentially continuous profile to an intermediate location at approximately one-half the depth, and a generally spherical surface portion extending inwardly from the intermediate location for the remainder of the depth, the frusto-conical surface portion making a shallow angle of about 6° with the axial direction; and providing the frusto-conical surface portions of the outer surface of the shell component and the inner surface of the prepared acetabulum with relative dimensions such that upon nesting of the spherical surface portions of the outer surface of the shell component and the inner surface of the prepared acetabulum in contiguous relationship, said frusto-conical surface portions will engage one another in an interference fit to secure the shell component within the prepared acetabulum.

14. The invention of claim 13 wherein the radius of the frusto-conical surface portion of the outer surface of the shell component at the lower rim thereof is slightly greater than the radius of the spherical surface portion of said outer surface, and the step of preparing the acetabulum includes forming the frusto-conical portion of the inner surface of the prepared acetabulum with a radius at the mouth thereof essentially equal to the radius of the spherical surface portion of the inner surface.

15. The invention of claim 14 wherein the difference between said radius of the frusto-conical surface portion of said outer surface and said radius of the frusto-conical surface portion of said inner surface is approximately 0.5 mm.

16. The invention of claim 14 wherein the step of preparing the acetabulum includes forming the generally spherical surface portion of the inner surface and subsequently forming the generally frusto-conical surface portion of the inner surface.

17. In the method of implanting an acetabular cup within a prepared acetabulum and securing the acetabular cup therein with an interference fit, the acetabular cup having an outer surface contour including a generally frusto-conical portion extending upwardly in an axial direction between a lower rim and an intermediate location spaced approximately one-half the distance between the lower rim and an upper top, and a generally spherical portion extending axially upwardly between the intermediate location and the upper top, the frusto-conical portion making a shallow angle of about 6° with the axial direction, the steps of:

preparing the acetabulum to provide a prescribed configuration having a mouth, a depth extending inwardly in an axial direction and corresponding to said distance between the lower rim, and the upper top, and an inner surface contour including a generally frusto-conical portion extending inwardly from the mouth along an essentially continuous profile to an intermediate location at approximately one-half the depth, and a generally spherical portion extending inwardly from the intermediate location for the remainder of the depth and having a radius corresponding to the radius of the spherical portion of the outer surface contour of the acetabular cup, the frusto-conical portion making a shallow angle of about 6° with the axial direction; and providing the frusto-conical portions of the outer surface contour of the acetabular cup and the inner surface contour of the prepared acetabulum with relative dimensions such that upon nesting of the spherical portions of said outer surface contour and said inner surface contour in contiguous relationship, said frusto-conical portions will engage one another in an interference fit to secure the acetabular cup within the prepared acetabulum.

18. The invention of claim 17 wherein the radius of the frusto-conical portion of the outer surface contour of the acetabular cup at the lower rim thereof is slightly greater than the radius of the spherical portion of said outer surface contour, and the step of preparing the acetabulum includes forming the frusto-conical portion of the inner surface configuration with a radius at the mouth thereof essentially equal to the radius of the spherical portion of the inner surface configuration.

19. The invention of claim 18 wherein the difference between said radius of the frusto-conical portion of said outer surface contour and said radius of the frusto-conical portion of said inner surface contour is approximately 0.5 mm.

20. The invention of claim 18 wherein the step of preparing the acetabulum includes forming the generally spherical portion of the inner surface contour and subsequently forming the generally frusto-conical portion of the inner surface contour.

* * * * *